(12) United States Patent
Chen et al.

(10) Patent No.: US 8,409,617 B2
(45) Date of Patent: Apr. 2, 2013

(54) VITAMIN POWDER COMPOSITION AND METHOD OF MAKING

(75) Inventors: Chyi-Cheng Chen, Binningen (CH); Bruno Leuenberger, Allschwil (CH)

(73) Assignee: DSM Nutritional Products Inc., Parsippany, NJ (US)

( * ) Notice: Subject to any disclaimer, the term of this patent is extended or adjusted under 35 U.S.C. 154(b) by 0 days.

(21) Appl. No.: 09/726,880

(22) Filed: Nov. 30, 2000

(65) Prior Publication Data

US 2001/0009679 A1    Jul. 26, 2001

(30) Foreign Application Priority Data

Dec. 9, 1999    (EP) ..................................... 99124519

(51) Int. Cl.
*A61K 9/14*    (2006.01)
*A61K 47/36*    (2006.01)
*A61K 47/42*    (2006.01)

(52) U.S. Cl. ......... 424/489; 424/464; 424/499; 424/500
(58) Field of Classification Search .................. 424/489, 424/499, 500, 464
See application file for complete search history.

(56) References Cited

U.S. PATENT DOCUMENTS

| | | | |
|---|---|---|---|
| 2,756,177 A * | 7/1956 | Cannalonga et al. ......... 264/109 |
| 2,824,807 A | 2/1958 | Laster et al. | |
| 3,138,532 A | 6/1964 | Aiello et al. | |
| 3,886,294 A | 5/1975 | Emodi et al. | |
| 3,971,852 A * | 7/1976 | Brenner et al. ................ 426/103 |
| 3,998,753 A * | 12/1976 | Antoshkiw et al. ............. 516/58 |
| 4,830,859 A * | 5/1989 | Finnan et al. .................. 424/465 |
| 4,844,924 A | 7/1989 | Stanley | |
| 4,935,245 A | 6/1990 | Horn et al. | |
| 5,120,761 A * | 6/1992 | Finnan .......................... 514/458 |
| 5,152,923 A | 10/1992 | Weder et al. | |
| 5,478,569 A | 12/1995 | Berneis et al. | |
| 5,607,707 A * | 3/1997 | Ford et al. ......................... 426/2 |
| 5,616,358 A | 4/1997 | Taylor et al. | |
| 5,668,183 A * | 9/1997 | Leuenberger ................. 514/168 |
| 5,938,990 A | 8/1999 | Boyle et al. | |
| 5,952,395 A * | 9/1999 | Lorant ........................ 514/772.4 |
| 5,968,251 A | 10/1999 | Auweter et al. | |
| 6,071,963 A * | 6/2000 | Tritsch et al. .................. 514/560 |
| 6,162,474 A * | 12/2000 | Chen et al. ....................... 426/72 |

FOREIGN PATENT DOCUMENTS

| | | | |
|---|---|---|---|
| EP | 0 239 086 A2 | | 9/1987 |
| EP | 0 347 751 A1 | | 12/1989 |
| EP | 0565 989 | * | 10/1993 |
| EP | 0 811 633 A2 | | 12/1997 |
| EP | 841010 A1 | * | 5/1998 |
| EP | 937412 A1 | * | 8/1999 |
| EP | 1 010 716 A2 | | 8/2000 |
| FR | 2 281 961 | | 3/1976 |
| GB | 490001 | | 8/1938 |
| GB | 743600 | | 1/1956 |
| GB | 760549 | | 10/1956 |
| GB | 1026493 | | 4/1966 |
| JP | 59/227243 | | 12/1984 |
| WO | WO 97/44009 | | 11/1997 |
| WO | WO 98/47464 | | 10/1998 |
| WO | WO 99/42134 | | 8/1999 |

OTHER PUBLICATIONS

Patent Abstracts of Japan, vol. 009, No. 096 of JP 59/227243 (1984).
Derwant English language abstract of EP 0 239 086 A1 (document B1 above).
Patent Abstracts of Japan, "Production of dried powder containing lipophilic vitamin and/or carotenoid," Publication No. 11-158063 (1999).
Pharmacie galenique—Bonnes pratiques de fabrication des medicaments, 7th ed., pp. 64-68, and 149-156.
Desrumaux & Marcand, "Formation of sunflower oil emulsions stabilized by whey proteins with high-pressure homogenization (up to 350 Mpa): effect of pressure on emulsion characteristics," Int'l. J. Food Sd. & Tech., vol. 37, pp. 263-269 (2002).
Derwent English language Abstract No. 0001054035, WPI Acc No: 1976-14935X/ of French Patent Publication No. 2 281 961 (1976).
Patent Abstracts of Japan: Japanese Laid-open Patent [Kokai]; Publication No. Hei 2-51594, published Feb. 21, 1990.
Japanese Patent [Kokoku] Publication No. Sho 35/9197 (1960).
Patent Abstracts of Japan: Japanese Laid-open Patent [Kokai] Publication No. Hei 11-196785, published Jul. 27, 1999.
Japanese Laid-open Patent [Kokai] Publication No. Hei 1-249716, published Oct. 5, 1999, Translation.

* cited by examiner

*Primary Examiner* — Lakshmi Channavajjala
(74) *Attorney, Agent, or Firm* — Baker Donelson Bearman Caldwell & Berkowitz, PC

(57) ABSTRACT

A powder composition containing at least one fat-soluble vitamin dispersed in a matrix of a natural polysaccharide gum or a mixture of gums having an emulsifying capacity and/or a protein or a mixture of proteins having an emulsifying capacity. The fat-soluble vitamin in the powder compositions is in the form of droplets having an average diameter in the range of about 70 to about 200 nm. Tablets, beverages and beverage concentrates, foods, cosmetics and pharmaceuticals containing the powder composition can be made.

21 Claims, 2 Drawing Sheets

The Effect of Emulsion Droplet Size on the Optical Clarity of Vit. E 15% SD and Vit. E 25% SD Water Dispersion

VITAMIN POWDER COMPOSITION AND METHOD OF MAKING

FIELD OF THE INVENTION

The present invention relates to new compositions, especially powder compositions and emulsion compositions, useful to produce nutritious vitamin and mineral supplemented beverages that contain vitamin E and other fat-soluble vitamins.

BACKGROUND OF THE INVENTION

Sports beverages such as GATORADE®, and vitamin supplemented waters, are beverages where the addition of vitamins is of interest. Also of interest are beverages used to restore electrolytes lost through diarrhea, for example, Pedialyte®. Also of interest are carbonated beverages such as flavored seltzer waters, soft drinks or mineral drinks, as well as non-carbonated fruit and vegetable juices, punches and concentrated forms of these beverages. In supplementing such beverages, it is often desirable to preserve the optical clarity of the beverage. Fat-soluble vitamins for supplementation are available in many forms, but when added to beverages, will tend to increase the visible turbidity. Ringing, i.e. the formation of a separate fat-soluble vitamin layer on the top of the liquid, is also a problem which is often encountered in fat-soluble vitamin fortification in beverages. One means of adding fat-soluble vitamins to beverages without significantly increasing turbidity or ringing is to encapsulate the vitamins in liposomes. However, this is a costly process, and the concentration of active substance in the liposome tends to be low.

SUMMARY OF THE INVENTION

One object of the present invention is to provide a powder composition of fat-soluble vitamins which can be added to beverages in a restorative or nutritionally supplemental amount, preferably without affecting the optical clarity of the beverage and without altering the sensory properties of the beverage to which it is added. In particular, the powder composition does not cause ringing and enhances the bioavailability.

Another object of the present invention is an emulsion composition comprising a fat-soluble vitamin, a matrix component as defined herein below, and water.

Another object of the present invention is a tablet containing the powder composition of this invention. The tablets of this invention may be dissolved in a liquid without causing ringing.

Another object of the present invention is a beverage, by which is meant liquids intended for human or animal consumption, containing the powder composition of this invention where the fat-soluble vitamins are present in a nutritionally supplemental or restorative amount. Another object of the present invention is a method for producing the powder composition.

Another object of the invention is a food product containing the powder composition of this invention.

Accordingly, one embodiment of the invention is a powder composition containing at least one fat-soluble vitamin, wherein a vitamin is dispersed in a matrix comprising an emulsion-forming composition selected from the group consisting of a natural polysaccharide gum, a mixture of polysaccharide gums, a protein, a mixture of proteins, and mixtures thereof, wherein the fat-soluble vitamin is present in the powder composition in the form of droplets having an average diameter of about 70 to about 200 nanometers (nm).

Another embodiment is an emulsion for preparing a powder composition that includes a fat-soluble vitamin droplets dispersed in a matrix component, wherein the droplets are about 70 to about 200 nm in diameter.

A further embodiment is a beverage having a liquid admixed with a powder composition containing at least one fat-soluble vitamin, wherein a vitamin is dispersed in a matrix containing an emulsion-forming composition selected from a natural polysaccharide gum, a mixture of polysaccharide gums, a protein, a mixture of proteins, and mixtures thereof, wherein the fat-soluble vitamin is present in the powder composition in the form of droplets having an average diameter of about 70 to about 200 nanometers (nm).

Another embodiment is a skin care product containing a powder composition having at least one fat-soluble vitamin, wherein a vitamin is dispersed in a matrix comprising an emulsion-forming composition selected from a natural polysaccharide gum, a mixture of polysaccharide gums, a protein, a mixture of proteins, and mixtures thereof, wherein the fat-soluble vitamin is present in the powder composition in the form of droplets having an average diameter of about 70 to about 200 nanometers (nm).

Another embodiment is a method for producing a powder composition, which method includes:

(a) combining water with a matrix component for a period of time sufficient for the matrix component to dissolve in the water to form a solution;

(b) adding a fat-soluble vitamin to the solution to form a crude emulsion;

(c) emulsifying the crude emulsion at a temperature of about 5° C. to about 75° C. at a pressure of about 10,000 psi (about 680 bar) to about 60,000 psi (about 4080 bar), to obtain a vitamin supplement emulsion consisting of droplets with average diameter sizes of 70-200 nm; and (d) drying the emulsion to obtain a powder composition.

Another embodiment is a composition to which a powder is admixed to form a product containing a fat soluble vitamin, wherein the powder has at least fat-soluble vitamin in the form of droplets of about 70 to 200 nm in diameter, which is dispersed in a matrix comprising an emulsion-forming material selected from the group consisting of a natural polysaccharide gum, a mixture of natural polysaccharide gums, a protein, a mixture of proteins, and a mixture of a polysaccharide gum and a protein.

DETAILED DESCRIPTION OF THE INVENTION

Figure 1:
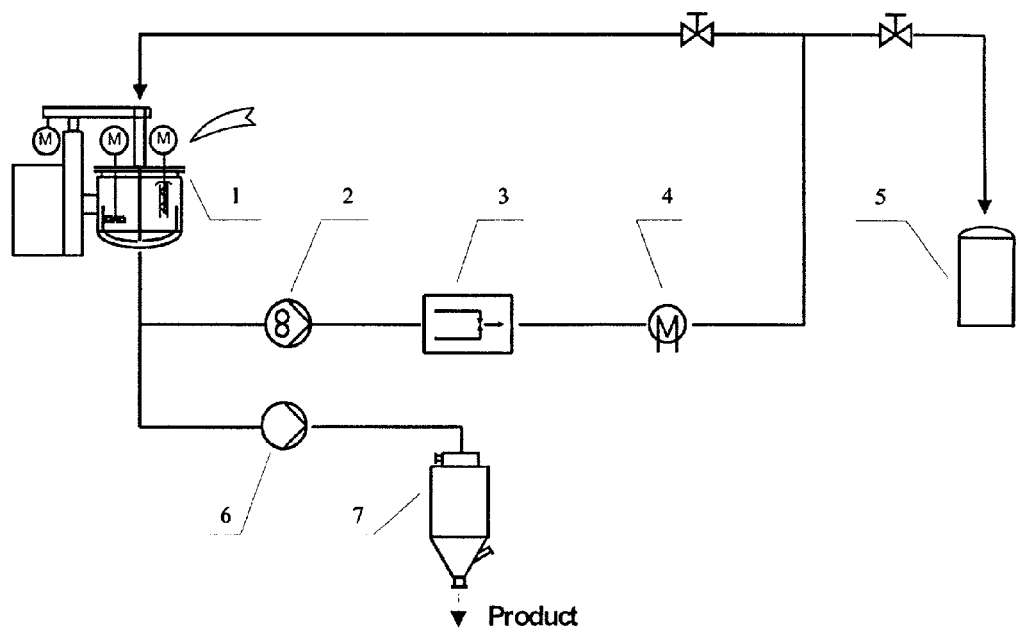
FIG. 1 shows a flow diagram of the typical procedure for preparation of a powder composition of this invention. 1—25 liter Fryma process unit with integrated dissolve disc and colloid mill; 2—gear pump. max. 1,000 liters/hr. max. 100 bar. 3—microfluidizer, M-210C-E/H, 100 liter/hr. max, 2,000 bar 4—heat exchanger with cold water (ca. 10° C.) 5—milk can 6—pump integrated to Minor spray dryer 7—spray dryer Minor Model Hi-Tec.

The present invention relates to a powder composition containing at least one fat-soluble vitamin characterized in that the vitamin is dispersed in a matrix of a natural polysaccharide gum or a mixture of gums having an emulsifying capacity and/or a protein or a mixture of proteins having an emulsifying capacity, and wherein the fat-soluble vitamin is present in the powder composition in the form of droplets having an average diameter within the range of about 70 to about 200 nanometers (nm), particularly about 70 to about 150 nm.

A preferred powder of this invention includes fat-soluble vitamin droplets with an average diameter within the range of about 80 to about 120 nm. Most preferred is an average droplet size of about 100 nm in diameter.

The powder composition may include a single vitamin, or more than one vitamin. The vitamin may be in pure foam, or it may be in a diluent such as an edible oil. Powder compositions of this invention contain vitamin droplets of a very small size. As a result, the compositions can be added to a liquid without causing ringing. In addition, bioavailability is improved. Also, preferred compositions of this invention may be added to a clear liquid without significantly increasing its turbidity.

The powder of this invention is made up of particles that include at least one fat-soluble vitamin dispersed in a matrix containing at least one natural polysaccharide gum or at least one protein with emulsifying capacity. The natural polysaccharide gum or the protein with emulsifying capacity, when used as matrix materials in the present invention, are also referred to as "matrix" or "matrix component(s)." These particles may be of various sizes, but all of them are at least sufficiently large to have a structure throughout which individual droplets of the fat-soluble vitamin are distributed. These particles may be as large as several hundred microns. The vitamin droplets have an average size within the range of about 70 to about 200 nm in diameter or even less. The droplets may contain a fat-soluble vitamin in a pure form, or a fat-soluble vitamin in a suitable medium or diluent such as an edible oil. The droplets may also contain a mixture of two or more different fat-soluble vitamins. When the powder is added to a liquid, the predominant structure of the resulting droplets within the liquid is a vitamin core sheathed by the matrix component interface between vitamin and the aqueous medium.

Droplet size is conveniently determined by a light scattering technique using an instrument such as Malvern ZetaSizer 3, which provides an average droplet size (the "Z" average). This method is known in the art and described in various references, for example in Particle Size Distribution, ACS Symposium Series 332, Ed. T. Provder, American Chemical Society, Washington, D.C. (1987). Thus, a powder composition of this invention contains droplets consisting of the fat-soluble vitamin with an average droplet size of about 70 to about 200 nm in diameter as measured by the technique of light scattering.

As used herein, the terms "droplet size" and "particle size" both refer to the diameter of the respective droplet or particle, unless otherwise specifically noted.

Optical clarity may be estimated by a visual comparison, such that if there is no significant visible added turbidity, the liquid has retained its optical clarity. Optical clarity (turbidity) can be accurately measured by a turbidimeter. To determine the turbidity, a sample is dispersed, with stirring, in water or a beverage. After complete dispersion, which usually takes a few minutes or more (up to complete dispersion as determined below), the turbidity of the resulting liquid is measured using a turbidimeter as is available from Orbeco Analytical Systems, Inc., Farmingdale, N.Y. Complete dispersion is indicated when a constant turbidity reading is obtained. Turbidity is measured by directing a beam of light into a cell containing the test sample, measuring the amount of light that is reflected at a 90 degree angle by any droplets present in the sample and comparing it to the light scattered by a standard reference suspension. The intensity of the light reflected at 90 degrees is measured by a suitable photodetector, amplified and displayed on a digital readout. The amount of reflected light is directly proportional to the degree of turbidity. NTU (Nephelometric Turbidity Unit) is customarily used to describe the results from the turbidity measurement using a turbidimeter. Higher NTU means higher turbidity.

Any standard turbidimeter will provide equivalent NTU measurements. For purposes of this invention, an NTU of ten or less is optically clear. For example, the NTU of most commercial apple juices investigated is about 5. An optically clear liquid to which a preferred powder composition of this invention has been added will preferably have a resulting NTU of no more than forty NTUs, and preferably ten to twenty NTUs. The compositions of this invention may also be added to liquids that are not optically clear. In this regard, increase in turbidity is not of concern. Ringing will not occur. Also, bioavailability of the vitamin may be increased. The invention contemplates powder compositions which, when added to a liquid, provide vitamin droplets averaging about 70 to about 200 nm in diameter, preferably about 70 to about 150 nm, more preferably about 80 to about 120 nm, and most preferably about 100 nm. When the liquid is optically clear, then the liquid remains for all practical purposes optically clear after addition of a powder composition according to this invention.

The natural polysaccharide gums and/or the proteins with emulsifying capacity as used in this invention are defined herein below. The polysaccharide gum and/or the protein, as used in this invention both have sufficient emulsifying properties. This means that they have sufficient emulsifying properties in an oil-in-water context to emulsify the oil into a fine dispersion in an aqueous medium and are capable of forming a stable emulsion of a desired droplet size (for example 70-200 nm) under conditions of high pressure homogenization. As used herein, "high pressure" means a pressure of about 10,000 psi (about 680 bar) to about 60,000 psi (about 4080 bar). Even higher pressures may be used, if required. Natural polysaccharide gums with emulsifying capacity and proteins to be used in the present invention are known and are commercially available, or may be isolated by a skilled person using conventional methods. Polysaccharide gums have been described for example in *Industrial Gums*, ($3^{rd}$ Ed., Academic Press, Inc., 1993).

Whether a selected polysaccharide gum or a protein to be used according to the present invention has an emulsifying capacity sufficient to be used for performing the present invention may be easily determined by assaying whether or not the selected polysaccharide gum and/or protein can maintain an emulsion as defined above, and as further described herein below.

Briefly, one starts with a crude emulsion made by dissolving the matrix component in a suitable aqueous solvent such as water and during homogenization adding fat-soluble vitamins in such proportions as to produce a crude emulsion with a solids content (percent by weight of vitamin(s) and matrix component) of preferably no more than 60%. A solids content of 70% is possible, however it may be difficult to process due to the thickness of the emulsion. The amount of lipid, or lipid content, is the lipid component of the solids content. The lipid component may be pure vitamin or vitamin in an appropriate diluent. The lipid content preferably makes up 75% by weight or less of the solids content. If the resulting emulsion has an average emulsion droplet size of about 70 to about 200 nm, after one cycle up to about one hundred cycles of emulsification (passes) at a pressure of about 10,000 to 60,000 psi (about 680 to about 4080 bar), then the matrix component is suitable to be used in this invention. The matrix component should also produce an emulsion that remains stable at least until the performance of the next preparation step, which preferably is spray drying.

Preferably, the matrix component should be at least acceptable for animal consumption. For human consumption, preferred matrix components should be GRAS (generally recognized as safe) or are an approved material for food consumption as determined by the various regulatory agencies worldwide.

As used herein, a "natural polysaccharide gum having an emulsifying capacity" is a polysaccharide gum which originates from plants, animals or microbial sources and which has not been intentionally subjected to chemical modifications to alter its chemical structure. All gums such as exudate gums, seaweed gums, seed gums or microbial gums may be used to perform the present invention provided they have an emulsifying capacity and, depending on the use contemplated, are at least acceptable for animal consumption or preferably are GRAS or are an approved material for food consumption as determined by the various regulatory agencies worldwide.

Examples of natural polysaccharide gums include gum arabic, flaxseed gum, ghatti gum, tamarind gum and arabinogalactan. Preferred are gum arabic, gum ghatti and arabinogalactan. Most preferred is gum arabic. These gums have a sufficient emulsifying action for use in the present invention. These gums lower the interfacial tension in oil-in-water emulsions and, at the same time, increase the viscosity of the aqueous phase.

Generally, it is difficult to handle aqueous solutions of polysaccharide gums at higher concentrations than 5%. There are, however, exceptions. Gum arabic, for example, dissolves rather quickly when stirred into water at concentrations higher than 5%. Quality grade of gum arabic yields colorless, bland-tasting solutions.

Industrial gums useful for carrying out the present invention may contain varying amounts of added substances such as inorganic salts. Product specifications often vary according to plant origin, production method or intended application. For the expert in the art, such variations are normal and present no problem in applying such gums according to the present invention.

The matrix component of the present invention may be a natural polysaccharide gum with emulsifying capacity. The natural polysaccharide gum may be mixed with a protein having emulsifying capacity or, alternatively, a protein alone having emulsifying capacity may be used as a matrix component wherein the fat-soluble vitamin is present in the form of droplets having an average diameter within the range of about 70 to about 200 nanometers (nm).

Proteins as used in the present invention are defined as polypeptides, which originate from plant or animal sources and possess emulsifying capacity, e.g. gelatine, plant proteins and milk proteins. Such proteins are known in the art. The proteins may be of vegetable (plant) or animal origin. Examples of such proteins include sunflower proteins, soybean proteins, cotton seed proteins, peanut proteins, rape seed proteins, milk proteins, blood proteins, egg proteins, and acetylated derivatives thereof, and gelatine or crosslinked gelatine. Preferred are gelatine and milk proteins. Gelatines may be extracted from skins or bones by acid or base hydrolysis, and therefore herein are not named "natural." In this sense, the term "gelatine" includes also suitable chemical derivatives thereof such as acetylated gelatine or crosslinked gelatine.

The matrix component may include a natural polysaccharide gum with emulsifying capacity or a mixture of different natural polysaccharide gums having emulsifying capacity without the admixture of any proteins. Alternatively, the matrix may include a protein with emulsifying capacity or a mixture of such proteins of different origins without the admixture of any natural polysaccharide gum.

The matrix may further include a mixture of (i) a natural polysaccharide gum with emulsifying capacity or a mixture of such natural polysaccharide gums of different origins together with (ii) a protein with emulsifying capacity or a mixture of such proteins of different origins. In this case, the ratio of component (i) to component (ii) is not critical and is a matter of optimization. Therefore, the ratio of component (i) to component (ii) may be within the ratio of 1:99 to 99:1. It is, however, preferred that the matrix include either a natural polysaccharide gum or a mixture of gums only as described or a protein or a mixture of proteins only as described. Potentially, interactions between polysaccharides and proteins may occur and, depending on the processing conditions, especially on the processing pH, may reduce or even destroy the emulsifying property. This is easily determined by one skilled in the art, who is able to choose the correct mixture and the optimized processing conditions when using such a mixture.

As fat-soluble vitamins, vitamin E or its esters (for example vitamin E acetate), vitamin A or its esters (for example vitamin A acetate and vitamin A palmitate), vitamin K (phytomenadione) and vitamin $D_3$ (cholecalciferol) are contemplated in the present invention. Vitamin E or its esters is the preferred fat-soluble vitamin, with vitamin E acetate being most preferred. Such vitamins are readily available from commercial sources. Also, they may be prepared by conventional methods by a skilled person. Vitamins may be used in pure form, or in a suitable diluent such as a fat or edible oil (e.g. soybean oil). Thus the droplets in the powder of this invention may contain one or more vitamins in a pure state or in an appropriate diluent.

Thus, a preferred powder composition includes droplets of a fat-soluble vitamin which are dispersed in a matrix component as described above, wherein (i) the droplets have an average diameter within the range of about 70 to about 200 nm, preferably about 70 to about 150 nm, more preferably about 80 to about 120 nm, most preferably about 100 nm;

(ii) the fat-soluble vitamin is selected from the group consisting of vitamin E or its esters, vitamin A or its esters, vitamin K, and vitamin $D_3$; and (iii) the matrix component includes a natural polysaccharide with emulsifying capacity gum or a protein with emulsifying capacity.

Most preferably, the fat-soluble vitamin is vitamin E acetate and the matrix is selected from gum arabic, gum ghatti, and gelatine, preferably from gum arabic or gelatine, and preferably from gum arabic.

The composition of this invention may include from about 0.5% to 75% by weight of fat-soluble vitamin (the "potency" of the composition) and from about 99.5% to 25% by weight of a matrix component, on a dry weight basis, the total weight of the components adding up to 100% by weight.

A preferred percent of fat-soluble vitamin is from about 15% to about 40%, most preferably about 25% by weight, based on the total weight of all the components present in the composition, whereby the composition as a final powder product usually has a moisture content of about 1-3% by weight.

The composition may contain only vitamin and matrix components in percentages that add up to 100%. The composition may also contain a small amount of residual water. The amount of residual water depends on the drying technology used, which will be evident to a skilled practitioner. A typical amount of residual water is up to about 4.0% by weight. Alternatively, other ingredients standard to a vitamin powder composition may be added. For example, vitamin protectors such as sucrose or maltodextrin alone or in combination, and/or antioxidants may be added. The amounts of vitamin and matrix component may then be adjusted accordingly. Part of this invention therefore is also a composition where the ratio of fat-soluble vitamin to matrix component is from about 1:99 to about 3:1. A preferred composition includes from about 15% to about 40% by weight of fat-soluble vitamin and from about 60% to 85% by weight of a matrix component. A preferred ratio of fat-soluble vitamin to matrix component is about 1:8 to 1:1, preferably about 1:5.7 to 1:1.5. In a particularly preferred composition, the fat-soluble vitamin is vitamin E or vitamin E acetate and the matrix component is gum arabic or gelatine, especially gum arabic.

Another embodiment of this invention is an emulsion composition which includes a fat-soluble vitamin; a matrix component as defined above, optionally a preservative and water, wherein the droplets of the emulsion are no more than about 70 to about 200 nanometers in diameter.

A preferred emulsion of 5% to about 20% by weight of the fat-soluble vitamin, preferably about 7.5% to about 20%; about 30% to 40% by weight of the matrix component, and about 50% to about 55% of water, wherein the weight-% of all the components add up to 100%.

This emulsion is useful for preparing the powder composition of the present invention. The preferred matrix component is as defined above. A preferred vitamin is vitamin E and its acetate. When other components such as preservatives are included, the percent vitamin, matrix component, and water is adjusted accordingly.

Tablets, in particular effervescent tablets, are part of the present invention. Such tablets include a fat-soluble vitamin and the matrix component as defined above, and are preferably obtained from a powder composition according to this invention and as described herein by formulating the composition into effervescent tablets by conventional tabletting means. When added to a liquid such as water, mineral water, or a beverage, the tablet dissolves and provides a liquid whose fat-soluble vitamin contents do not cause ringing, by which is meant separation of a top fat-soluble vitamin layer on the liquid. The tablets of this invention may be produced from any powder composition described herein, for example compositions wherein the preferred matrix is a gum as defined above, especially gum arabic, arabinogalactan, gum ghatti, or gelatine, preferably gum arabic and a preferred vitamin is vitamin E and its acetate.

This invention is also directed to a beverage containing a powder composition or an emulsion as described above. The present invention is also directed to beverages containing a mixture of:

(i) a matrix component as defined above, and a nutritionally supplemental amount of a fat-soluble vitamin in the form of droplets which average from about 70 to about 200 nm in diameter, preferably about 70 to about 150 nm in diameter; and (ii) a liquid containing juice and/or water, and, optionally, a flavor, to bring the beverage weight to 100%.

Preferred are beverages as described above, wherein (i) the fat-soluble vitamin is selected from the group of vitamin E or its esters, vitamin A or its esters, vitamin K, and vitamin $D_3$; and (ii) the matrix is a gum or a protein as described above, especially gum arabic, arabinogalactan, gum ghatti, or gelatine, preferably gum arabic or gelatine.

Most preferred is a beverage wherein the fat-soluble vitamin is vitamin E acetate and the matrix is gum arabic or gelatine. A preferred amount of the vitamin in such a composition is from about 2 to 12 mg of vitamin E per 100 grams of liquid. An especially preferred amount is 3.2 to 8.0 mg of vitamin E per 100 grams. Most preferred is about 6.0 mg per 100 grams.

The liquid for a typical beverage may be about 3% (wt) fruit juice and 97% (wt) water, or 0.05% (wt) flavor, 1.95% (wt) fruit juice, and 98% (wt) water. Sweeteners, pre-servatives, stabilizers, and other known beverage components may be included in the beverage. When these components are included, the percentage of juice, flavor, and water are adjusted accordingly.

In the case of clear beverages, the preferred beverage should have an optical clarity which does not differ significantly from its optical clarity before addition of the powder, for example, which does not appear significantly more turbid on visual inspection.

This invention is also directed to a beverage including a mixture of:

(i) a nutritionally supplemental amount of a fat-soluble vitamin, and a matrix component as defined herein above, (ii) a liquid containing juice and/or water, and, optionally, a flavor, to bring the beverage weight to 100%, and (iii) which beverage has an optical clarity of no more than 20 NTUs when containing up to 6 mg of vitamin per 100 g of liquid.

The beverages of this invention are preferably obtained by adding to a beverage a powder composition of this invention. Adding a powder composition of this invention to a liquid requires no special procedure or extensive mixing. The powder may simply be added to the liquid and mixed by shaking or stirring until the powder particles are no longer visible to the naked eye. One or more of the powder compositions of this invention may be added to a beverage as described herein, to obtain a beverage, e.g. a fortified beverage. For example, the fat-soluble vitamin may be one or more of vitamin E or its esters, vitamin A or its esters, vitamin K, and vitamin $D_3$, especially vitamin E and vitamin E acetate. The matrix may be as defined above including the preferred matrix components.

Fat-soluble vitamins may be added in a restorative amount, i.e. in an amount sufficient to replace the vitamin naturally present in a beverage such as juice or milk, which vitamin has been lost or inactivated during processing. Fat-soluble vitamins may also be added in a nutritionally supplemental amount, i.e. in an amount considered advisable for a child or adult to consume based on RDAs and other such standards, preferably from about one to three times the RDA (Recommended Daily Amount). A nutritionally supplemental amount of fat-soluble vitamin may be readily determined by a skilled person to obtain the desired amount of fortification in a liquid, e.g. a beverage, and based on RDAs and other such standards. A preferred amount of vitamin E is from about 2 to 12 mg of vitamin E per 100 grams of liquid. An especially preferred amount is 3.2 to 8.0 mg per 100 grams of liquid. Most preferred is about 6.0 mg per 100 grams of liquid. Thus, the powder compositions of this invention may be added to a beverage to provide a vitamin E concentration of from about 2 to 12 mg or 3.2 to 8.0 mg per 100 grams of liquid. In the case of fat-soluble vitamins which have greater potency than vitamin E, it is preferred to formulate the powder composition such that 2 to 12 mg of such a vitamin per 100 grams in diluent (e.g. edible oil) may be added. This means that the vitamin is diluted in diluent so that 2 to 12 mg of vitamin per 100 g in diluent provides a suitable nutritionally supplemental amount, for example a multiple of the RDA, preferably 1 to 3 times the RDA. For example, the RDA for vitamin $D_3$ is 400 IU. Thus, a vitamin $D_3$ composition of this invention would preferably contain 15% to 40% by weight of 400 IU of vitamin $D_3$ in diluent. The same would apply to other fat-soluble vitamins. Alternatively, the vitamin itself in undiluted form may be used to make the powder composition. Whether or not dilution is necessary will depend on the potency of the vitamin.

The amount of powder composition to be added depends on the potency of the powder, i.e. the amount of vitamin in the powder, which in this invention can range from about 0.5% to about 75% by weight. Preferred powders have a potency of about 25% (wt) to about 40% (wt). Powders with smaller droplet sizes will in general generate less turbidity in liquid. Based on the droplet size and the desired level of fortification and turbidity, the skilled person should be able to determine the amount of powder to add, depending on its potency, to attain desired optical clarity. If a beverage to be supplemented is already turbid, then an increase in NTUs is less likely to be of concern, and a higher range of added turbidity can be accommodated.

The beverages of this invention may be carbonated beverages, e.g. flavored seltzer waters, soft drinks or mineral drinks, as well as non-carbonated juices, punches and concentrated forms of these beverages. Beverages, especially juice and cola beverages, which are carbonated in the manner of soft drinks, as well as "still" beverages, nectars, and full-strength beverages or beverage concentrates which contain at least about 45% by weight of juice are also contemplated.

The fruit juices and fruit flavors used herein include grape, pear, passion fruit, pineapple, banana or banana puree, apricot, orange, lemon, grapefruit, apple, cranberry, tomato, mango, papaya, lime, tangerine, cherry, raspberry, carrot, and mixtures thereof. Additionally, artificial flavors, e.g. cola, or natural flavors derived from these juices may be used in the beverages. Chocolate flavors and other non-fruit flavors may also be used to make beverages containing the vitamin and mineral supplement. Additionally, milk, obtained from cows or synthetic, is a contemplated beverage to which the powder compositions of this invention may be added. The milk may itself include other beverage components, in particular flavors such as chocolate, coffee, or strawberry. As used herein, the term "juice product" refers to both fruit and vegetable juice beverages, and fruit and vegetable juice concentrates which comprise at least about 45% (wt) fruit juice. As used herein, the term "vegetable" means both nonfruit, edible plant parts, such as tubers, leaves, rinds, and also, if not otherwise indicated, any grains, nuts, beans, and sprouts which are provided as juices or beverage flavorings.

Sport beverages are also contemplated as beverages which can be supplemented by the powder compositions of the present invention. Typical sport beverages contain water, sucrose syrup, glucose-fructose syrup, and natural or artificial flavors. These beverages may also contain citric acid, sodium citrate, and monopotassium phosphate, as well as other materials which are useful in replenishing electrolytes lost during perspiration.

As used herein, the term "juice beverage" refers to a fruit or vegetable juice product which is in a single-strength, ready-to-serve, drinkable form. Juice beverages of the present invention may be of the "full-strength" type which typically contain at least about 95% (wt) juice. Full strength juice beverages also include those products of 100% (wt) juice such as, for example, orange, lemon, apple, raspberry, cherry, apricot, pear, grapefruit, grape, lime, tangerine, carrot, pineapple, melon, mango, papaya, passion fruit, banana and banana puree, cranberry, tomato, carrot, cabbage, celery, cucumber, spinach, and various mixtures thereof. Juice beverages also include extended juice products which are referred to as "nectars." These extended juice products typically comprise from about 50% (wt) to about 90% (wt) juice, preferably from about 50% (wt) to about 70% (wt) juice. Nectars usually have added sugars or artificial sweeteners or carbohydrate substitutes. As used herein, the term "citrus juice" refers to fruit juices selected from orange juice, lemon juice, lime juice, grapefruit juice, tangerine juice, and mixtures thereof.

As used herein, the term "juice materials" refers to concentrated fruit or vegetable juice, plus other materials such as juice aroma and flavor volatiles, peel oils, and pulp or pomace. As used herein, the term "juice concentrate" refers to a fruit or vegetable juice product which, when diluted with the appropriate amount of water, forms drinkable juice beverages. Juice concentrates within the scope of the present invention are typically formulated to provide drinkable beverages when diluted with 3 to 5 parts by weight water.

As used herein the term "beverage concentrate" or "bottling syrup" refers to a mixture of flavors, water and from about 10% (wt) to about 60% (wt) sugar or carbohydrate substitute, i.e. sucrose, dextrose, corn syrup solids, fructose, dextrins, polydextrose, and mixtures thereof.

The flavor component of the beverages and beverage concentrates contains flavors selected from fruit flavors, vegetable flavors, botanical flavors and mixtures thereof. As used herein, the term "fruit flavor" refers to those flavors derived from the edible reproductive part of a seed plant, especially one having a sweet pulp associated with the seed, and "vegetable flavor" refers to flavors derived from other edible parts of the seed and other plants. Also included within the term "fruit flavor" and "vegetable flavor" are synthetically prepared flavors made to simulate fruit or vegetable flavors derived from natural sources. Particularly preferred fruit flavors are the citrus flavors including orange, lemon, lime and grapefruit flavors. Besides citrus flavors, a variety of other fruit flavors may be used, such as apple, grape, cherry, pineapple, mango, papaya flavors, and the like. These fruit flavors may be derived from natural sources such as juices and flavor oils, or may be synthetically prepared. As used herein, the term "botanical flavor" refers to flavors derived from parts of a plant other than the fruit, i.e. derived from nuts, bark, roots and leaves, and beans such as coffee, cocoa, and vanilla. Also included within the term "botanical flavor" are synthetically prepared flavors made to simulate botanical flavors derived from natural sources. Examples of such flavors include cola, tea, coffee, chocolate, vanilla, almond, and the like. Botanical flavors may be derived from natural sources such as essential oils and extracts, or may be synthetically prepared.

The flavor component may include a blend of various flavors, e.g. lemon and lime flavors, cola flavors and citrus flavors to form cola flavors, etc. If desired, juices such as orange, lemon, lime, apple, grape, carrot, celery, and like juices may be used in the flavor component. The flavors in the flavor component are sometimes formed into emulsion droplets which are then dispersed in the beverage concentrate. Because these droplets usually have a specific gravity less than that of water and would therefore form a separate phase, weighting agents (which may also act as clouding agents) are typically used to keep the emulsion droplets dispersed in the beverage. Examples of such weighting agents are brominated vegetable oils (BVO) and rosin esters, in particular the ester gums. See L. F. Green, *Developments in Soft Drinks Technology*, Vol. 1, (Applied Science Publishers Ltd. 1978), pp. 87-93, for a further description of the use of weighting and clouding agents in liquid beverages.

Besides weighting agents, emulsifiers and emulsion stabilizers may be used to stabilize the emulsion droplets. The particular amount of the flavor component effective for imparting flavor characteristics to the beverages and beverage concentrates ("flavor enhancing") may depend upon the flavor(s) selected, the flavor impression desired, and the form of the flavor component. The flavor component may include at least 0.05% by weight of the beverage composition, and typically from 0.1% to 2% by weight for carbonated beverages. When juices are used as the flavor, the flavor component may include, on a single-strength basis, up to 25% fruit juice by weight of the beverage, preferably from 5% to 15% juice by weight for carbonated beverages.

Carbon dioxide may be introduced into the water which is mixed with the beverage syrup or into the drinkable beverage after dilution to achieve carbonation. The carbonated beverage may be placed into a container, such as a bottle or can, and is then sealed. Any conventional carbonation methodology may be used to make the carbonated beverages of this invention. The amount of carbon dioxide introduced into the beverage will depend upon the particular flavor system used and the amount of carbonation desired. Usually, carbonated beverages of the present invention contain from 1.0 to 4.5 volumes of carbon dioxide. The preferred carbonated beverages contain from 2 to about 3.5 volumes of carbon dioxide.

The present invention is also particularly suited for the supplementation of beverages and beverage concentrates, including citrus juices. The beverages may contain from 3% (wt) to 100% (wt) juice or from about 0.05% (wt) to about 10% (wt) of an artificial or natural flavor, particularly orange juice. The concentrated orange juice, orange juice aroma and flavor volatiles, pulp and peel oils used in the method of the present invention may be obtained from standard orange juice. See Nagy et al, *Citrus Science and Technology*, Volume 2, (AVI Publishing Co. 1977), pp. 177-252 for standard processing of oranges, grapefruit and tangerines. (See also Nelson et al, *Fruit and Vegetable Juice Processing Technology* (3rd Ed., AVI Publishing 1980), pp. 180-505 for standard processing of noncitrus juices such as apple, grape, pineapple, etc. to provide sources of juice and juice materials for noncitrus juice products).

Juices from different sources are frequently blended to adjust the sugar-to-acid ratio of the juice. Different varieties of oranges may be blended or different juices may be blended to get the desired flavor and sugar-to-acid ratio. A sugar-to-acid ratio of from about 8:1 to about 20:1 is considered acceptable for fruit juices. However, preferred sugar-to-acid ratios are typically from about 11:1 to about 15:1, especially for citrus juices.

Sweeteners include the sugars normally present in juice products, for example glucose, sucrose, and fructose. Sugars also include high fructose corn syrup, invert syrup, sugar alcohols, including sorbitol, refiners syrup, and mixtures thereof. In addition to sugar, extended juice beverages of the present invention may contain other sweeteners. Other suitable sweeteners include saccharin, cyclamates, acetosulfam, and L-aspartyl-L-phenylalanine lower alkyl ester sweeteners (e.g. aspartame). A particularly preferred sweetener for use in such extended juice products is aspartame. For single-strength juice beverages, the sugar content may range from about 2° to about 16° Brix (16° Brix means the juice contains about 16% soluble solid, and so on). Typically, the sugar content of such beverages depends upon the amount of juice contained therein. For full-strength beverages containing at least about 95% (wt) juice, the sugar content is typically from about 5° to about 14° Brix. For extended juice beverages which contain from about 50% (wt) to about 90% (wt) juice, the sugar content is typically from about 5° to about 13° Brix (no other sweetener) or from about 2° to about 8° Brix (other sweetener containing). For juice concentrates according to the present invention, the sugar content may range from about 6° to about 75° Brix. Typically, the sugar content of these juice concentrates is from about 20° to about 50° Brix. For orange juice concentrates, the sugar content is preferably from about 35° to about 50° Brix.

The amount of the sweetener effective in the beverages of the invention depends upon the particular sweetener used and the sweetness intensity desired. For noncaloric sweeteners, this amount varies depending upon the sweetness intensity of the particular sweetener. For sugar, this amount can be from 1% to 14% (typically from 6% to 14%) by weight for carbonated beverages. Preferred beverages contain from 9% to 13% by weight sugar. In determining the amount of sugar for beverages of the present invention, any sugar or other sweetener present in the flavor component, such as in juice, is also included. Low-calorie sweetener combinations containing a noncaloric sweetener, such as aspartame, and a sugar, such as high fructose corn syrup, may also be used in beverages. For beverage syrups, the amount of sugar in a beverage syrup is from about 10% (wt) to about 60%(wt) and preferably from about 40% (wt) to about 60% (wt). In addition to sweeteners, beverages may also already be fortified with water soluble or fat-soluble vitamins. The composition of this invention may be added to beverages that already contain or to which are later added vitamin compositions that are not of this invention.

The various beverage and beverage concentrates may be packaged in conventional packages for the particular beverage or beverage concentrates which are nutritionally supplemented by the optically clear composition of fat-soluble vitamins. In some instances, the concentrates are frozen.

The powder compositions of this invention may also be added to cosmetics, if it is desired, to blend fat-soluble vitamins such as vitamin E into a cosmetic. If the cosmetic is optically clear, preferred compositions of this invention may be used to avoid increasing the turbidity of the cosmetic. Cosmetics include any materials designed for application to the skin, hair, or nails, for example skin care products such as balms, lotions, or sticks, various ointments, make-up compositions for use on the face, eyes, or lips, shampoos and conditioners, nail polishes, and the like. The cosmetic may contain other active ingredients as used in the cosmetics industry. Pharmaceutical compositions intended for topical application in the form of ointments, lotions, and the like are also contemplated. Cosmetic formulations will be well known to the skilled person. The powder composition of this invention is added at an appropriate time in the production process such as to be thoroughly blended into the cosmetic.

The powder composition of this invention which contains droplets of a fat-soluble vitamin that average about 70 to about 200 nanometers in diameter (preferably about 70 to about 150 nm, more preferably about 80 to about 120 nm, and most preferably about 100 nm), and which are dispersed in a matrix as defined herein above may be made by:

(a) combining water with a matrix as defined herein above for a period of time sufficient for the matrix component to dissolve in the water;

(b) adding a fat-soluble vitamin to the solution of step (a) to form a crude emulsion, preferably a crude emulsion having a solids content as described above, preferably of from about 30% (wt) to about 50% (wt), more preferably of about 45% (wt);

(c) mixing the crude emulsion of step (b) until the size of the droplets within the emulsion is determined to be about 1500 nm or less;

(d) emulsifying the crude emulsion of step (c) at a temperature of about 5° C. to about 75° C. at a pressure of about 10,000 to about 60,000 psi (about 680 to about 4080 bar), preferably of about 25,000 psi (about 1700 bar) to obtain a vitamin supplement emulsion consisting of droplets with average sizes of about 70 to about 200 nm in diameter; and (e) drying the emulsion of step (d) to obtain a powder composition which contains droplets of a fat-soluble vitamin that average about 70 to about 200 nanometers in diameter, and which are dispersed in the matrix component.

Step (a) may be done at any reasonable temperature to ensure a rapid dissolution of the matrix component in water and to fully utilize its functionality. To ensure complete dissolution of the matrix component within a reasonable amount of time (i.e., sufficient for the matrix component to dissolve), heating to about 70° C. or 80° C. is preferable, after which the resulting solution may be conveniently cooled to about room temperature or a little higher (about 30° C.).

In order to attain the desired droplet size, the emulsion step (d) may be repeated through one or more passes as necessary to obtain the desired droplet size, i.e. the crude emulsion is passed into the homogenization vessel, emulsified, passed out of the to homogenization vessel, and passed through the homogenization vessel again until the desired droplet size is attained. Usually at least five to twenty passes will be required. These passes are usually all performed at the same pressure and the same system parameters, but different pressures may be used for different passes (other system parameters could also be varied for different passes).

The period of time for one pass is not critical. The amount of time per pass will depend on system parameters including emulsion viscosity, batch size, flow rate and pressure. These parameters will depend on the precise processing format selected, and may be varied by the skilled person to obtain the desired results. Emulsification passes should continue until testing shows that the desired droplet size is achieved as determined by particle size analysis (for example, by light scattering as described above).

It is important that the homogenization step be performed at an ultra-high pressure as described above to effectively reduce the droplet size of the emulsion to a desirable size. The homogenization temperature as measured at the exit of the homogenizer is preferably below 70° C. The emulsion is then converted to a powder, by a known technology such as freeze-drying, fluid-bed drying, beadlet formation, but preferably by spray-drying, to obtain a powder composition which includes droplets of a fat-soluble vitamin which droplets average about 70 to about 200 nm in diameter (preferably about 70 to about 150 nm, more preferably about 80 to about 120 nm, and most preferably 100 nm), and which are dispersed in a matrix of natural polysaccharide gum or of protein. A powder composition produced by this process is part of this invention.

The final emulsion yields a powder which, upon redispersal in a liquid, yields an emulsion droplet (diameter) size generally about 5-15 nm larger than the droplet size of the emulsion before spray drying. A powder so produced will contain vitamin droplets e.g. of 200 nm diameter or less. Such a powder when added to a liquid, will provide droplets with average droplet size of about 70 to about 200 nm in diameter, preferably about 70 to about 150 nm in diameter, most preferably about 100 nm in diameter. Such droplet sizes are convenient for adding to beverages at fortification levels of up to about 2 to about 12 mg, preferably about 3.2 to about 8 mg and especially about 6 mg of vitamin per 100 g of beverage. As discussed above, vitamin E may be added in pure form (i.e. 6 mg of vitamin E per 100 g). However, the more potent fat-soluble vitamins will preferably be diluted, so that what is added would be 6 mg of vitamin in diluent, rather than 6 mg of pure vitamin. When added, the resulting beverage should display no ringing. In addition, the added vitamin may be provided with superior bioavailability.

Figure 2:
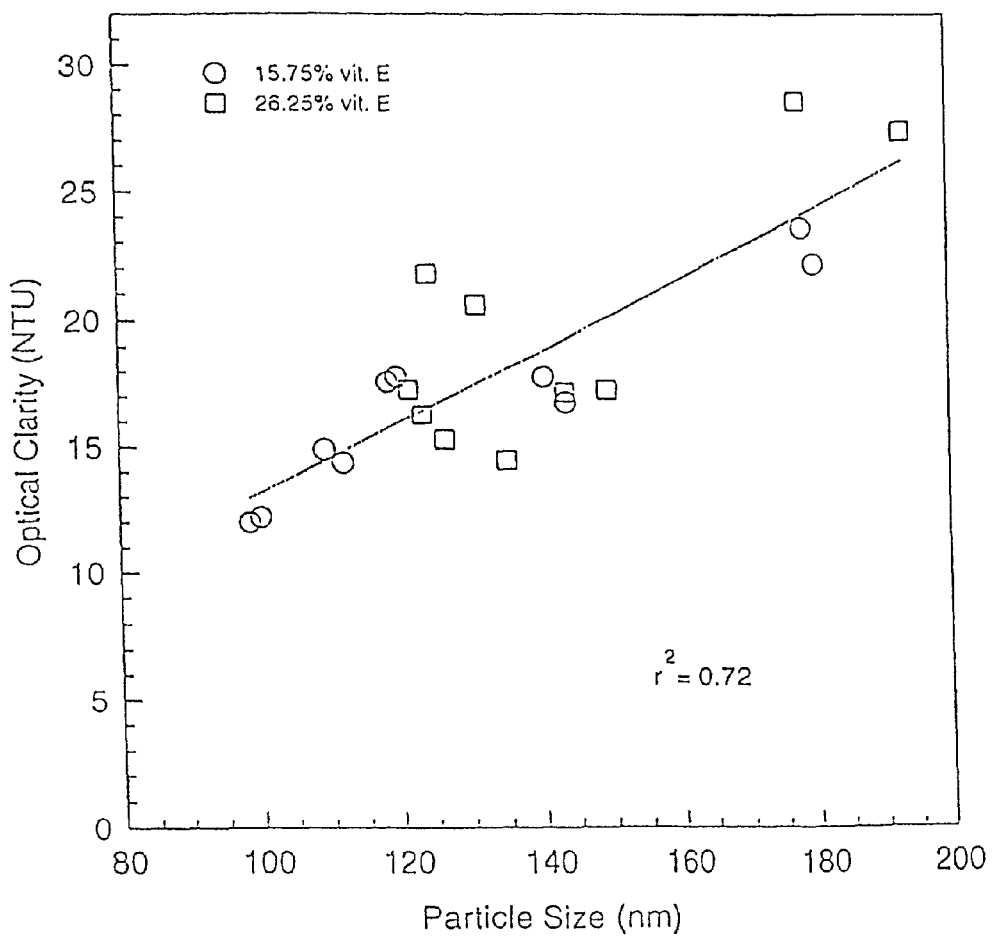
FIG. 2 shows a graph of droplet size (nm) versus optical clarity (NTU) for 15.75% (wt) vitamin E (circle) and 26.25% (wt) vitamin E (square) in water dispersion.

With regard to an originally optically clear beverage, in order to maintain optical clarity, a preferred composition of this invention may be added. The NTU of the resulting beverage should be no more than 30, and preferably around 10 to 15, especially at lower levels of fortification. In general, at the desired levels of fortification a droplet size of about 120 nm in diameter is acceptable with regard to optical clarity, and does not contribute substantial NTUs. In general, a droplet of smaller size may be preferable for use at a higher level of fortification. Thus, with regard to minimizing turbidity in an optically clear beverage, a powder with a higher average vitamin droplet size would be more useful at a lower level of fortification, while a powder with a lower average vitamin droplet size would be preferable at a higher level of fortification. In this regard, FIG. 2 provides guidance on the relationship between droplet size and optical clarity. As can be seen by this best fit approximation, this relationship is roughly linear such that as droplet size increases, NTU increases for the same level of fortification. Thus, optical clarity (NTU) is a function of the droplet size of the composition.

To obtain the emulsion and powder of this invention, the parameters of the above process may be varied within the limits provided. The pertinent variables are pressure and temperature in the emulsification step, solids content, which is percent by weight of the vitamin(s) plus the matrix component in the crude emulsion, the lipid component of the solids content, which is the percent by weight of the solids content which is vitamin(s), including any edible diluent such as oil, and the number of passes through the emulsification step. Within the guidance of this invention, these parameters may be varied to obtain a powder composition which contains vitamin droplets of e.g. 200 nm or less in diameter, and which has a potency (which is percent by weight of vitamin) of from about 0.5% to 75%, especially about 25% to about 40%, and which provides fortification levels of multiple RDAs of the vitamin, preferably about 1-3 RDA of vitamin, most preferably in the form of 5 to about 30 mg of vitamin (pure, or as processed in a diluent) per 8 ounces of liquid.

The potency of the powder of this invention is determined by the amount of fat-soluble vitamin in the crude emulsion. For example, an emulsion which is about 5% to about 15% by weight vitamin (pure vitamin or vitamin in diluent) will in rough estimate provide a powder with a potency of about 10% to 30% by weight. However, a skilled person will be able to vary the emulsion content with the guidance provided by this invention to obtain a desired potency in the resulting powder.

In general, the lower the pressure, the more passes will be required to obtain an emulsion with a given droplet size. Also, the higher the lipid content, the more passes will be required to obtain the given droplet size. As discussed above, the droplet size of the emulsion determines the droplet size in the resulting powder, and the droplet size in the liquid to which the powder is ultimately added is about 5-15 nm greater than the droplet size of the original emulsion. The potency of the powder is roughly twice the lipid content (for pure vitamin) of the emulsion. The emulsion is processed as described above, and in more detail below, to obtain the desired droplet size. If a high level of fortification is desired, then it is preferable to obtain a powder with droplet sizes at the low end of the range. Lower droplet sizes can be obtained by increasing the processing pressure, or the number of passes. If it is possible to increase the processing pressure, then a given number of passes at the higher pressure will provide smaller droplets. However, if the pressure cannot be increased (if for example 15,000 psi (1020 bar) is the upper limit for the equipment being used), then the same result can be obtained by increasing the number of passes.

With regard to obtaining a powder containing droplets of a size which provide an acceptable turbidity for the desired fortification level, the droplet size resulting from addition of the powder is the most important variable. It is possible to add less of a higher potency powder than of a lower potency powder to get the same level of fortification, but if the higher potency powder has a larger droplet size, then the fact that less of this powder is added will not negate the effect of the droplet size and higher turbidity will result.

To obtain powder compositions of this invention, the above parameters may be varied within the following limits: The pressure range is from about 10,000 psi (about 680 bar) to about 60,000 psi (about 4080 bar), preferably from about 20,000 psi (about 1360 bar) to about 35,000 psi (about 2380 bar), and especially about 30,000 psi (about 2040 bar). The solids content is preferably no more than 60% (wt). A preferred crude emulsion has a solids content of from about 30% (wt) to about 50% (wt), preferably about 45% (wt), a preferred lipid content is from about 10% (wt) to about 50%.(wt) A preferred potency is from about 25% (wt) to about 40% (wt). The number of passes that will be required to attain a droplet size in the emulsion of about 70 to about 200 nm may be adjusted depending on the parameters.

The various steps in the above method may be performed by known methods using conventional reagents and equipment. A skilled person given the guidance provided herein will be able to adjust the emulsion, solids and lipid content (for potency), pressure, temperature, and number of passes, within the limits of this invention, to readily obtain a powder composition of this invention.

In more detail, the powder is prepared by emulsifying a crude emulsion of fat-soluble vitamin and matrix component (for example the emulsion of this invention). Once the emulsion has reached the desired emulsion droplet size, it is spray dried into a powder. The potency of the powder is the weight percent of vitamin which the powder contains.

The crude emulsion is prepared by homogenizing the fat-soluble vitamin with the aqueous matrix component in suitable amounts which will provide a powder product having a droplet size when dissolved in liquid of about 70 to about 200 nm, preferably about 70 to 150 nm, more preferably about 80 to about 120 nm and most preferably about 100 nm. An emulsion containing about 5-15% by weight of fat-soluble vitamin, 30-40% by weight of matrix component, and 50-55% by weight water is an example. The emulsion may be prepared in a standard vessel of a convenient capacity where heating and cooling can take place. The water and matrix component are added to the vessel. The mixture may be heated to about 80° C., but this is not required. The mixture should be stirred until the matrix component has dissolved.

The solution is then left at or cooled to room temperature, i.e., to about 30° C., and the fat-soluble vitamin is slowly added. The mixture is homogenized to a crude emulsion in the vessel (for example by using a colloid mill or any other conventional mixing means) until the droplet size is less than 1500 nm. Droplet size may be measured by any conventional particle size analyzer. A preferred measuring technique is the laser light scattering technique. The Malvern ZetaSizer 3 or Autosizer Iic (Malvern Instruments, Southborough, Mass.) is an example of a laser light scattering measuring device that is used to measure particle size according to the present invention.

The crude emulsion is then further emulsified using standard equipment and vessels for this purpose. The device selected should provide a sufficiently high pressure. Microfluidizer devices are useful, models such as M-210C-E/H, M-110ET, M-610-C, and M-140K, may be obtained from Microfluidics International Corporation, Newton, Mass. It is also possible to use a water jet (such as those produced by Jet Edge Inc., Minneapolis, Minn.). The crude emulsion may be transferred from the holding vessel to the emulsifying device through a suitable sieve in order to prevent clogging of the microfluidizer. The temperature at which the homogenization (by which is meant further emulsification) takes place is best kept between room temperature (about 20-25° C.) or about 30° C. up to about 75° C. with a cooling system such as an ice water bath to control the temperature of the emulsion. The pressure pump of the emulsifying device should be set at a suitable pressure. Note that pressure in the device may fluctuate over a wide range, depending on the number of pistons in the high pressure pump. A two-piston Microfluidizer may vary, e.g. from 7,250 to 14,500 psi (500 to 1000 bar). A three-piston pump is preferable.

Homogenization continues for a sufficient number of passes to obtain an emulsion of the desired droplet size. In general, the more stable the process pressure, the fewer number of passes should be required to achieve the same droplet size. The emulsion is then dried to obtain the powder of this invention. Drying may be accomplished by any standard method, for example spray-drying in a suitable spray dryer, such as a Yamato Mini-Spray Dryer.

The following examples are provided to further illustrate the compositions and processes of the present invention. These examples are illustrative only and are not intended to limit the scope of the invention in any way.

EXAMPLES

Example 1

Gum arabic (Example 1a), and gelatine (Example 1b) in an amount of 10 kg was dissolved in 23.3 kg distilled water at a temperature up to 80° C. The solution was then cooled to about 30° C. Vitamin E acetate (1.87 kg) was gradually added and, at the same time, homogenized until the droplet size of the emulsion was below 1500 nm. The crude emulsion was then homogenized with a high pressure homogenizer (Microfluidics International Corporation, Newton, Mass.). The emulsion was recycled through the homogenization process until the droplets of the emulsion reached an average size of below 140 nm. During the homogenization, the temperature of the emulsion was maintained at about 35° C. with a cooling system.

The emulsion was then spray-dried with a spray dryer to yield a powder containing about 15% (wt) of vitamin E acetate. When the powder was used in beverage fortification, the turbidity of the beverages did not increase significantly and also no phase separation occurred, that is, the vitamin E acetate lipid phase did not separate from the aqueous phase and form a layer on the surface.

The amount of powder to be added to a beverage depends on the amount of fortification desired. It is important to determine the optimal particle size for the desired level of fortification.

The beverage or beverage concentrates supplemented with the compositions or tablets of fat-soluble vitamins of the present invention may be made by conventional means well known to those of ordinary skill in the art. In general, the optically clear composition of fat-soluble vitamins may be simply added and gently mixed into the beverage or beverage concentrates or syrups. The effervescent tablet is generally dropped into the beverage and allowed to dissolve (tablets do not generally yield an optically clear beverage due to other tabletting ingredients, but do yield a beverage without ringing, provided that other ingredients do not themselves cause ringing). The beverage concentrates and syrups to which the powder composition of fat-soluble vitamins has been added may be used to make a final single strength beverage by blending the concentrate or syrup with an appropriate amount of water, usually about 1 part concentrate or syrup to about 3 to 4 parts of water. The water may be carbonated or non-carbonated.

Examples of other beverages, to which the powder compositions of fat-soluble vitamins as produced in Examples 1a) or 1b) may be added in nutritionally supplemental amounts, include:

(c) "sparkling" orange juice containing 55% (wt) orange juice and 45% (wt) carbonated water;

(d) pear-grapefruit nectar containing 25% (wt) pear juice, 20% (wt) grapefruit juice, the balance containing 10% (wt) sucrose-water;

(e) kiwi-grapefruit drink containing 20% (wt) kiwi fruit juice, 15% (wt) grapefruit juice, the balance containing water;

(f) mixed fruit "cocktail" containing 10% (wt) each of the juices of passion fruit, mango, guava, pineapple, papaya, banana, apricot, mandarin orange, pear and lime juices;

(g) yogurt/fruit beverage containing 20% (wt) milk products, 1% (wt) pectin, 20% (wt) pineapple juice, 10% (wt) shredded pineapple fruit pulp, 16% (wt) corn syrup, the balance containing water;

(g) cola beverage containing 0.35% (wt) cola flavor emulsion, 11% (wt) sugar, 0.1% (wt) phosphoric acid, 0.1% (wt) citric and malic acids, caramel coloring, the balance containing carbonated water;

(i) full-strength orange juice;

(j) full-strength apple juice; and (k) full-strength flavored cow's milk.

Example 2

Effervescent Tablets

Tablets were produced from the powder of Examples 1a) at 26.24% (wt) and Example 1b) at 42.5% (wt) and compared with tablets produced from a current 50% (wt) vitamin E powder product (see Table 1). The 50% (wt) vitamin E powder used for comparison was obtained from Roche Vitamins and Fine Chemicals, Nutley, N.J.

The formulation shown in Table 1 was chosen for the test. In this formula, after the dissolution of the tablets (from dry Vitamin E 50% (wt) powder, Type CWS/F), very small oil droplets of vitamin E may be seen on the surface of the water, if the surface is observed against reflected light.

TABLE 1

Effervescent Tablet

| | Composition | Label Claim Mg | Overage % (wt) | E 26.25% Quantities mg/Tabl. | E 42.1% Quantities mg/Tabl. | E 50.0% Quantities mg/Tabl. |
|---|---|---|---|---|---|---|
| 1 | Beta-Carotene | 6.00 | 20 | | | |
| | as Beta Tab 10% E | | | 72.00 | 72.00 | 72.00 |
| 2 | Vitamin C | 200.00 | 10 | | | |
| | as Ascorbic Acid, Fine Granular | | | 220.00 | 220.00 | 220.00 |
| 3 | Vitamin E | 50.00 | 10 | | | |
| | as Dry Vitamin E 26.25% SD Lot 27903-076 | | | 209.52 | | |
| | as Dry Vitamin E 42.1% SD Lot 27903-076 | | | | 130.64 | <110 |
| 4 | Citric Acid Anhydrous, Medium Granular | | | 1300.00 | 1300.00 | 1300.00 |
| 5 | Sodium bicarbonate | | | 800.00 | 800.00 | 800.00 |
| 6 | Sodium carbonate | | | 80.00 | 80.00 | 80.00 |
| 7 | Mannitol MG[1] | | | 1138.48 | 1217.36 | 1238.00 |
| 8 | Aspartame | | | 20.00 | 20.00 | 20.00 |
| 9 | Sodium cyclamate | | | 30.00 | 30.00 | 30.00 |
| 10 | Polyethylene Glycol 6000 Fine Powder[2] | | | 100.00 | 100.00 | 100.00 |
| 11 | Orange flavor Permaseal 74016-71[3] | | | 20.00 | 20.00 | 20.00 |
| 12 | Tangerine flavor Permaseal 74740-31[3] | | | 10.00 | 10.00 | 10.00 |
| | Total Tablet Weight | | | 4000.00 | 4000.00 | 4000.00 |

Suppliers
[1]Mannitol medium granular, Roquette Frères, 4 rue Patou, F-59022 Lille Cédex, France
[2]Hoechst AG, Postfach 800320 Frankfurt/Main 80, F.R. Germany
[3]Givaudan Dübendorf AG, CH-8600 Dübendorf, Switzerland Procedure I. Pass 3-12 through 1.00 mm sieve and mix with 1 and 2 for 15 minutes.

II. Compress into effervescent tablets.

Results

Both samples tested gave tablets from the 26.25% (wt) and 42.5% (wt) vitamin E powders of this invention with acceptable hardness and disintegration characteristics. Their compression profiles are very close to that of E 50% CWS/F.

Sample 27903-076 containing 42.5% (wt) vitamin E showed better hardness and slightly shorter disintegration time than the other.

On visual inspection of the surface of the water after the disintegration of the tablets made from the 26.25% (wt) and 42.5% (wt), vitamin E powders of this invention did not show any oily droplets. In contrast, oily droplets were visible on the surface of the water with the vitamin E 50% CWS/F product not made from a composition of this invention.

Example 3

A vitamin conditioning shampoo is produced using standard ingredients and methods as follows using a powder composition of this invention. Vitamin E acetate powder as produced in Example 1a) and Example 1b) is used as follows: Disperse the vitamin E acetate powder as produced in Example 1a) or Example 1b) into water. Add the vitamin E acetate powder of Example 1a) or Example 1b) to a mixture of Monamid and phytantriol. Add the panthenol and etyl panthenol. Add Part 2 to Part 1 and mix until clear. Add the Kathon CG and perfume. Adjust the pH with citric acid 50% solution to pH 6.0 to 6.8. Adjust the viscosity with sodium chloride.

| Ingredients | CTFA designation | % by weight |
| --- | --- | --- |
| Part 1 | | |
| Deionized water | Water | 57.05 |
| Monamid 716 | Lauramide DEA | 5.00 |
| liquid DL-panthenol-50% | Panthenol and water | 2.00 |
| 25% vitamin E acetate powder | Tocopheryl acetate | 0.80 |
| Phytantriol | Phytantriol | 0.10% |
| Part 2 | | |
| Standapol ES-2 | sodium laureth sulfate | 30.00 |
| Mirataine CBS | Cocamidopropyl hydroxysultaine | 3.00 |
| Part 3 | | |
| Sodium chloride | sodium chloride | 1.00 |
| Citric acid 50% solution | citric acid | 0.30 |
| Perfume | Fragrance | 0.20 |
| Kathon CG | Methylchloroisothiazolinone (and) methylisothiazolinone | 0.05 |
| | Total: | 100 |

The invention being thus described, it will be obvious that the same may be varied in many ways. Such variations are not to be regarded as a departure from the to spirit and scope of the invention and all such modifications are intended to be included within the scope of the following claims.

What is claimed is:

1. A powder composition consisting of at least one fat-soluble vitamin dispersed in a matrix consisting of an emulsion-forming composition selected from the group consisting of a natural polysaccharide gum, a mixture of polysaccharide gums, a protein, a mixture of proteins, and mixtures thereof, wherein the fat-soluble vitamin is present in the powder composition in the form of solid droplets having an average diameter of about 80 to about 120 nanometers (nm) and wherein the fat-soluble vitamin is present in the powder composition in the amount of from about 10% to about 30% by weight and wherein the composition has a moisture content of about 1 to 4% by weight.

2. The powder composition according to claim 1 wherein the polysaccharide gum is isolated from the group consisting of plants, animals and microbial sources.

3. The powder composition according to claim 2 wherein the polysaccharide gum is selected from the group consisting of exudate gums, seaweed gums, seed gums, microbial gums, and mixtures thereof.

4. The powder composition according to claim 2 wherein the polysaccharide gum is selected from the group consisting of gum arabic, flaxseed gum, ghatti gum, tamarind gum, arabinogalactan, and mixtures thereof.

5. The powder composition according to claim 4 wherein the polysaccharide gum is gum arabic.

6. The powder composition according to claim 1 wherein the protein is isolated from a plant or an animal source.

7. The powder composition according to claim 6 wherein the protein is selected from the group consisting of sunflower proteins, soy-bean proteins, cotton seed proteins, peanut proteins, rape seed proteins, milk proteins, blood proteins, egg proteins, gelatine, crosslinked gelatine, and mixtures thereof.

8. The powder composition according to claim 7 wherein the protein is gelatine.

9. The powder composition according to claim 1 wherein the fat-soluble vitamin is selected from the group consisting of vitamin E or its esters, vitamin A or its esters, vitamin K (phytomenadione), vitamin $D_3$ (cholecalciferol), and mixtures thereof.

10. The powder composition according to claim 9 wherein the fat-soluble vitamin is selected from the group consisting of vitamin E acetate, vitamin A acetate, vitamin A palmitate, and mixtures thereof.

11. The powder composition according to claim 1 wherein the ratio of fat-soluble vitamin to matrix component is from about 1:99 to about 3:1.

12. The powder composition according to claim 11 wherein the ratio of fat-soluble vitamin to matrix component is from about 1:8 to 1:1.

13. The powder composition according to claim 1 wherein the composition comprises from about 60 to 85% by weight of a matrix component, based on the total weight of all the components present in the composition.

14. The powder composition according to claim 1, which is formed into a tablet.

15. The powder composition according to claim 1 wherein the emulsion-forming composition is an oil-in water emulsion-forming composition.

16. A powder composition consisting of at least one fat-soluble vitamin dispersed in a matrix of an emulsion-forming composition selected from the group consisting of a natural polysaccharide gum, a mixture of polysaccharide gums, a protein, a mixture of proteins, and mixtures thereof, wherein the fat-soluble vitamin is present in the powder composition in the form of solid droplets, wherein the powder composition is produced by a process comprising:

(a) combining water with a matrix component selected from the group consisting of a natural polysaccharide gum, a mixture of polysaccharide gums, a protein, a mixture of proteins, and mixtures thereof, to form a solution;

(b) adding a fat-soluble vitamin to the solution to form a crude emulsion, wherein the fat-soluble vitamin is added in an amount to provide from about 10% to about 30% by weight fat-soluble vitamin in the powder composition;

(c) emulsifying the crude emulsion at a temperature of from about 5° C. to about 75° C. at a pressure of from about 10,000 psi (about 680 bar) to about 60,000 psi (about 4080 bar), to obtain an emulsion in which the droplets have an average diameter of about 80 to about 120 nm; and (d) drying the emulsion to obtain the powder composition.

17. The powder composition according to claim 16, wherein the crude emulsion formed has a solids content of from about 30% (wt) to about 50% (wt).

18. The powder composition according to claim 16, further comprising mixing the crude emulsion prior to emulsifying, to provide a crude emulsion having droplets which are about 1500 nm or less.

19. The powder composition according to claim 16, wherein the emulsifying occurs at a pressure of from about 20,000 psi (about 1,360 bar) to about 35,000 psi (about 2380 bar).

20. The powder composition according to claim 16, wherein the emulsifying occurs at a pressure of about 25,000 psi (about 1,700 bar).

21. The powder composition according to claim 16 wherein the emulsion-forming composition is an oil-in water emulsion-forming composition.

* * * * *